ns Patent [19]

United States Patent [19]  
Courty et al.

[11] 3,975,302  
[45] Aug. 17, 1976

[54] SUPPORTED CATALYST FOR OXIDIZING METHANOL TO FORMALDEHYDE AND ITS MANUFACTURING PROCESS

[75] Inventors: Philippe Courty, Nanterre; André Sugier; Jean-François Le Page, both of Rueil Malmaison, all of France

[73] Assignee: Institut Francais du Petrole, des Carburants et Lubrifiants et Entreprise de Recherches et d'Activities Petrolieres Elf, Ruell-Malmaison, France

[22] Filed: Sept. 3, 1974

[21] Appl. No.: 502,842

[30] Foreign Application Priority Data  
Sept. 12, 1973 France .............................. 73.32874

[52] U.S. Cl. ........................... 252/455 R; 252/458; 252/462; 252/465; 252/470; 260/603 R
[51] Int. Cl.² .................. B01J 21/04; B01J 21/12; B01J 23/84

[58] Field of Search ................ 252/455 R, 458, 465, 252/470, 462; 260/603 R

[56] References Cited  
UNITED STATES PATENTS

| | | | |
|---|---|---|---|
| 2,474,440 | 6/1949 | Smith et al. | 260/603 R |
| 2,812,308 | 11/1957 | Shelton et al. | 252/470 X |
| 3,716,497 | 2/1973 | Courty | 252/470 |

Primary Examiner—W. J. Shine  
Attorney, Agent, or Firm—Millen, Raptes & White

[57] ABSTRACT

Process for manufacturing a supported catalyst whose active phase contains mainly molybdenum and iron by impregnating a carrier with an aqueous solution of alkanolamine and a complex of the active phase elements, drying and thereafter roasting the impregnated carrier.

50 Claims, No Drawings

SUPPORTED CATALYST FOR OXIDIZING METHANOL TO FORMALDEHYDE AND ITS MANUFACTURING PROCESS

This invention concerns new catalysts deposited on supports, whose active phase consists mainly of molybdenum and iron oxides, these catalysts being useful particularly for methanol oxidation to formaldehyde by means of molecular oxygen.

The invention also concerns a process for manufacturing said catalysts.

It is already known that the combination of molybdenum and iron oxides in proportions of $MoO_3/Fe_2O_3$ from about 3 to 10 is active for the oxidation of methanol to formaldehyde.

Various non-supported catalysts are used in industrial plants but, generally, they have the disadvantage of an insufficient mechanical strength. In order to improve the latter and also to reduce the cost of these catalysts, for improving their intergranular transfer properties and decreasing the filling density in industrial reactors, it is particularly advantageous to manufacture supported catalysts; however, various attempts have been made for depositing molybdenum and iron elements on carriers, but they did not lead to satisfactory results, particularly due to the fact that no convenient process could be developed for preparing impregnation solutions containing molybdenum and iron, while avoiding the precipitation of iron molybdate. Particularly, the solubilization in a mixture of water and alkanolamine which has been suggested, particularly in the U.S. Pat. No. 2,650,906, in the case of precipitates of cobalt-molybdenum, nickel-tungsten or tungsten-cobalt compounds, is inoperative in the case of precipitates of molybdenum-iron compounds. Thus, in most of the methods for the preparation of supported molybdenum-iron catalysts, the carrier is impregnated either by means of suspended precipitates (in this case, the particles of insoluble precipitates cannot penetrate the smallest pores of the carrier and the major portion of the metal compounds is deposited on the external macrosurface of the carrier particles) or by means of separate solutions for each metal element to be deposited, with intermediary drying and roasting, (in this case, even if the precipitation may be partly avoided, the deposited active phase is far from being sufficiently homogeneous). There has also been described in British Pat. No. 1,282,949 a process for manufacturing new solid complexes containing as principal metal elements, molybdenum containing anions and ferric ions which can be used as catalyst precursors for oxidizing methanol to formaldehyde. These solid complexes are in the form of homogeneous, amorphous and transparent gels, in which are mainly associated the anions $MoO_4^{2-}$ and $NO_3^-$, the cations $Fe^{3+}$ and $NH_4^+$ (from an ammonium molybdate and ferric nitrate in an atomic ratio of Mo/Fe in the range of 1.5 to 5) and a variable water amount. According to the teaching of the above-mentioned patent, such gels are obtained by adding first, under mechanical stirring and at a hourly rate by volume lower than 6, 300 ml per liter and per hour, an aqueous solution of ferric nitrate at a concentration between 1 gram-atom of iron per liter and the saturation concentration maintained at a temperature between its freezing point and 20°C, to a solution of ammonium molybdate at a concentration from 1 to 2.5 gram-atoms of molybdenum per liter, also maintained at a temperature between its freezing point and 20°C, said solutions being used in relative amounts corresponding to the atomic ratio of molybdenum to iron which it is desired to obtain in the final product.

There is thus obtained a paste composition which is transformed to an opaque rigid substance, and then, matures to a transparent amorphous solid gel. In the above-mentioned patent, provision is also made for the optional replacement in the ferric nitrate solution of up to 50% of the ferric ions by an equivalent atomic amount of simple cations selected from those of cobalt, nickel, manganese, chromium, scandium, yttrium and rare earth metals.

In British Pat. 1,282,950 a variant of said method is described, which consists of performing, by mechanical trituration, the reaction between mainly a solid ammonium molybdate (or freshly precipitated molybdic anhydride) and solid ferric nitrate, in the presence of a small water amount, smaller than the sum of the amounts necessary to form saturated solutions of the reactants, and at a temperature between the freezing point of said saturated solutions and 150°C, the reactants being used in relative amounts corresponding to the atomic ratio of molybdenum to iron which it is desired to obtain in the final product. In this way, there is formed a viscous solution or a homogeneous paste which, after maturation, becomes a transparent and amorphous solid gel.

In each of the above-mentioned British Patents, the provision is made for the optional replacement in the ammonium molybdate solution or in the mixture of solid reactants, of up to 50 % of the molybdenum anions by an equivalent atomic amount of oxygen-containing ions selected from those of chromium, tungsten, manganese, vanadium and uranium.

It has now been discovered, surprisingly, that solid gels containing, as principal elements, molybdenum and iron, and which are the object of the above-mentioned British Patents, have the property of being soluble up to large concentrations in mixtures of water with alkanolamines.

The present invention has therefore as an object a process for depositing, by impregnation, on a carrier, combinations of molybdenum and iron oxides, in a quite sufficiently homogeneous state and at a relatively high concentration.

It is also an object of the invention to provide supported catalysts whose active phase mainly comprises a combination of molybdenum and iron oxides and which have very good catalytic properties, particularly for oxidizing methanol to formaldehyde, as well as excellent mechanical and physical properties.

Thus, the supported catalysts of the invention are obtained by a process which comprises an original step of solubilizing elements to be used as an active phase of the catalyst, followed with a step of impregnating the carrier, drying and roasting, said last three operations being conducted under usual conditions.

The preparation of the impregnation solution essentially consists of adding to a mixture of water and of at least one alkanolamine, a convenient amount of amorphous solid gel such as hereinbefore defined.

Among the alkanolamines which are convenient for the preparation of the impregnation solution, are primary alkanolamines such for example as ethanolamine, amino-propanols and butanols, secondary alkanolamines such as diethanolamine or still tertiary alkanolamines such as triethanolamine. Ethanolamine which is easily available and inexpensive, is preferred.

Other alkanolamines may, however, also be used, such for example as 1,2-dihydroxy-3-amino propane or 1,2,3,4,5-pentahydroxy-6-amino hexane and, more generally, the primary, secondary or tertiary alkanolamines containing from 2 to 12 carbon atoms.

The alkanolamine concentration of the water-alkanolamine mixture must be sufficient for ensuring the complete dissolution of the molybdenum-iron gel amount which is to be introduced into the impregnation solution. Thus, according to the solubilizing method of the invention, it is possible, for example, by making use of water-alkanolamine mixtures containing up to about 700 g of alkanolamine per liter of mixture, to dissolve amounts of molybdenum-iron solid gel which, expressed in weight of molybdenum and iron oxides, may be as high as about 1,000 g per liter of solution. When making use of such solutions for the impregnation of a carrier having a pore volume of about 50 ml per 100 g, the resulting final catalyst, after drying and calcination, may have an active phase content as high as about 35 % by weight.

In most cases, use is made of water-alkanolamine mixtures whose alkanolamine content is from 300 to 600 g per liter of mixture, in which it will be possible to dissolve molybdenum-iron gel in amounts which, expressed as oxides, range from about 100 to 500 g per liter of solution.

The carrier used in the second step of the process may be selected from the usual carriers for the considered type of catalysis. It may have a pore volume from about 30 to 100 ml per 100 g and a specific surface from about 1 to 20 m²/g. It may be selected in a wide range and may, for example, consist of alumina, silica, alumina-silica, magnesia, alumina-magnesia, magnesia-silica, alumina-magnesia-silica.

The preferred carriers for performing the invention are α-alumina or calcinated clays; they are optionally stabilized by tungsten, magnesium, titanium, chromium, iron or molybdenum oxides, for example at concentrations of about from 1 to 10 % by weight.

A particularly preferred carrier consists of kaolinite, calcinated at a temperature from 600° to 900°C (metakaolin). The carriers may be shaped as balls or extrudates or still consist of powders.

The impregnation of the carrier by the molybdenum-iron gel solution may be conducted according to any usual technique; we may for example mix the powdered carrier with the impregnating solution, dry and roast the resulting product and then, put it in its final shape; we may also impregnate the previously shaped carrier with the impregnation solution.

The impregnated carrier is then dried, for example at a temperature from 50° to 150°C for 1 to 4 hours, then roasted for example at a temperature from 300° to 450°C for 1 to 4 hours.

It has also been discovered that, in addition to the amorphous gels such as described in the above-mentioned British Patents, it was possible to dissolve in mixtures of water with alkanolamine, iron molybdate precipitates, treated in accordance with the method described in U.S. Pat. No. 3,716,497, in which an iron molybdate precipitate is kneaded with an ammonium salt solution in an amount corresponding to 0.5–2 moles of ammonium salt per gram equivalent of iron in the precipitate, the ammonium salt being preferably a nitrate.

The dissolution of the so-treated iron molybdate precipitates is however not so easy as that of the amorphous gels and the use of the latter is preferred according to the invention.

The catalysts obtained by such a process as above described, may have an active phase content of, for example, from 5 to 35 % and, more particularly, from 10 to 20 % by weight.

Their mechanical strength, expressed in kg/mm for the catalysts in the form of extrudates, and in kgF for the catalysts in balls, is quite satisfactory. For the first ones, it is from 1 to 5 kg/mm (average measurement made with 20 extrudates) and, for the second ones, it is greater than 10 kgF. Surprisingly, the mechanical strength of the resulting catalysts is always greater than that of the corresponding carriers.

The catalysts of the invention can be used for the oxidation of methanol to formaldehyde by means of molecular oxygen under the usual conditions. For example, in a multitube reactor, the feed charge, consisting of an air-methanol mixture containing from 6 to 8 % by volume of methanol with respect to air, may be passed over the catalyst in fixed bed heated at a temperature of 250°–350°C, at a hourly rate by volume of 5,000 to 12,000 liters per liter of catalyst and per hour.

Very high conversion rates of methanol are thus obtained together with high formaldehyde yields.

The following examples are given for illustrating the invention, but are not intended in any way to limit the scope of the invention to the particular specific details described therein.

In these examples, the carriers were the following:

CARRIER A

It consists of α-alumina balls available in the trade under reference SCS.9 (manufactured by Société Française des produits pour catalyse), and has the following characteristics:

| | |
|---|---|
| Na₂O content | <1000 ppm |
| Balls diameter | 2.4–4 mm |
| Pore volume | 50 ml per 100g |
| Specific surface | 10–20 m²/g |
| Grain to grain crushing | extreme values 8–15 kg average value 12.5 kg |

CARRIER B 1,000 g of alumina balls SCS.9 are impregnated with 450 ml of an aqueous solution containing 120.7 g of ammonium metatungstate at a 92 % WO₃ concentration. After drying and roasting at 400°C for 2 hours, we obtain the carrier B, whose characteristics are as follows:

| | |
|---|---|
| WO₃ content | 9.8 % by weight |
| pore volume | about 48 ml per 100 g |
| specific surface | 12 m²g⁻¹ |
| grain to grain crushing | extreme values: 7–14.5 kg average value: 12 kg |

CARRIER C 2,000 g of kaolinite are malaxed with 100 g of starch and 50 g of ammonium nitrate preliminarily dissolved in 1,000 ml of water. The resulting paste is extruded to cylinders having a diameter and a height of 4 mm. The latter are placed in an oven at 100°C for one night, then calcined for 3 hours at 850°C. The resulting carrier has a porosity of about 50 ml per 100 g and a specific surface of about 10 m²/g. The grain to grain crushing, measured on the ERWEKA machine, is about 0.8 kg/mm.

CARRIER D 1,800 g of kaolinite and 300 g of hydrated magnesia (corresponding to 200 g of anhydrous MgO) are kneaded with 80 g of starch, 850 ml of water and 30 ml of commercial nitric acid ($d = 1.38$).

The resulting paste is treated as above indicated in relation with the manufacture of carrier C. We obtain a carrier D having a porosity of 53 ml per 100 g and a specific surface of about 12 m²/g. The grain to grain crushing, measured on the ERWEKA machine, is 0.6 kg/mm.

CARRIER E 1.850 g of kaolinite and 324 g of α-titanic acid gel (corresponding to 120 g of $TiO_2$) are malaxed with 100 g of starch, 900 ml of water and 50 ml of nitric acid. The resulting paste is treated as above indicated in relation with the preparation of carrier C. We obtain a carrier (E) having a porosity of 48 ml per 100 g, a specific surface of 16 m²/g and a mechanical strength of 0.7 kg/mm.

The mixed compounds containing iron and molybdenum which have been used, have been prepared as follows:

PRODUCT I

According to the method described in British Pat. No. 1,282,949 500 ml of a 2M solution of ferric nitrate nonahydrate preliminarily cooled down to about 15°C are reacted with 1,000 ml of a 2M/7 solution of tetrahydrated ammonium paramolybdate, preliminarily cooled to about 12°C. The resulting product, after hardening (1 hour at 20°C and 30 minutes at 45°C) is dehydrated in an oven at 65°C for 24 hours. We obtain a drak-brown colored vitreous substance, crystallographically amorphous, containing 60 % by weight of iron and molybdenum oxides expressed as $Fe_2O_3$ and $MoO_3$, the atomic ratio of Mo to Fe being 2.

PRODUCT II

According to the method described in British Pat. No. 1,282,950 we admix in a mortar 353.2 g of ammonium paramolybdate tetrahydrate (2 moles of $MoO_3$), 56.4 g of ammonium metatungstate at a $WO_3$ concentration of 92.05 % (0.222 mole of $WO_2$), 526 g of ferric nitrate nonahydrate (1,300 ion.g Fe3+) and 60.6 g of cobalt nitrate hexahydrate (0.208 ion.g Co2). The resulting pink-yellow paste is malaxed for 15 minutes at 20°C and then 30 minutes at 20 to 60°C and finally one hour at 60°C (in a WERNER malaxator). The paste is extruded to cylinders which are dried for 20 hours at 70°C. We obtain a dark-brown colored vitreous substance, crystallographically amorphous, containing 60 % by weight of molybdenum-tungsten-iron-cobalt oxides.

PRODUCT III

According to the method described in U.S. Pat. No. 3,716,497, we dissolve into 4 liters of water, 200 g of tetrahydrate ammonium paramolybdate (1.13 mole of $MoO_3$), the pH of the solution (solution A) being adjusted to a value from 4.5 to 5; the solution is heated to 60°C.

Separately, we dissolve 164 g of ferric nitrate (0.405 ion-gram Fe3+) into 2,200 ml of water, the pH of the solution (solution B) being adjusted to a value from 1 to 1.5 and the solution being maintained at room temperature.

We slowly add solution B to solution A under vigorous stirring; after decantation of the precipitate, the supernatent liquid is siphoned and then the precipitate is washed with 4 liters of water, filtrated and the precipitate (which contains, in a complex form, 0.405 ion/g $Fe^{3+}$) is admixed with 80 g of ammonium nitrate (1.00 mole); the ammonium salt is slowly dissolved in the water accompanying the precipitate. We obtain 784 g of compound III having, as shown by analysis a content by weight of 22.5 % of iron and molybdenum oxides, 10.2 % of $NH_4NO_3$ and 67.3 % of water.

The products of I to III, as above described, have been solubilized in the following conditions:

SOLUBILIZATION OF PRODUCT I

We dissolve 440 g of product I, previously crushed, into a solution of 290 g of monoethanolamine and 220 g of water. We obtain 650 ml of a solution (S1) containing 405 g/l of molybdenum-iron compound, expressed as oxides (Mo/Fe = 2).

SOLUBILIZATION OF PRODUCT II

We dissolve 320 g of product II, preliminarily crushed into a solution of 120 g of monoethanolamine, 30 g of diethanolamine and 220 g of water. We have obtained 470 ml of a solution (S2) containing 407 g/l of molybdenum-tungsten-iron-cobalt compound, expressed as oxides:

$$\frac{Mo + W}{Fe + Co} = 1.5 \text{ and } \frac{W}{Mo + W} = \frac{Co}{Fe + Co} = 0.10$$

SOLUBILIZATION OF PRODUCT III

We have dissolved 784 g of product III (at 67.3 % of $H_2O$) into 318 g of monoethanolamine. We have obtained 1,100 ml of a solution (S3) containing 160 g/l of molybdenum-iron compound, expressed as oxides (Mo/Fe ≈ 2.5).

By impregnation of carriers A–E in the conditions indicated in table I, we have prepared various catalysts some characteristics of which, particularly the mechanical strength, are also given in table I.

The resulting catalysts have been tested for oxidation of methanol to formaldehyde in a pilot unit comprising a number of tubes having an inner diameter of 17 mm and a length of 2 m, heated with oil (DOWTHERM) at a temperature from 250° to 320°C, according to the activity of the tested catalysts.

The catalysts, consisting either of extrudates of a length and diameter of about 3.5–3.8 mm (carrier C–E), or of balls of 2.4 – 4 mm of diameter (carriers A and B) are charged into the tubes. We send over the catalyst a gaseous air-methanol mixture at a methanol concentration of 6.5 % by volume in the air, at a hourly rate by volume of 10,000 volumes per volume of catalyst and per hour.

In table II, the conversion rate (C), selectivity (S) and yield (R) are defined as follows:

$$C = \frac{\text{converted methanol}}{\text{charged methanol}}$$

-continued $$S = \frac{\text{methanol converted to formaldahyde}}{\text{converted methanol (formaldehyde + CO + CO}_2)}$$

$$R = \frac{\text{obtained formaldehyde}}{\text{introduced methanol}}$$

measured in a stabilized state, i.e. after 1,000 hours of operation.

adding, under mechanical stirring and at an hourly rate by volume lower than 6,300 ml per liter and per hour, an aqueous solution of ferric nitrate at a concentration in the range of from 1 gram-atom of iron per liter and to the saturation concentration, maintained at a temperature between its freezing point and 20°C, to an ammonium molybdate solution at a concentration from 1 to 2.5 gram-atoms of molybdenum per liter, main-

TABLE I

| EX | CARRIER | GRAIN TO GRAIN CRUSHING (Kg/mm) | CARRIER WEIGHT (g) | IMPREGNATION SOLUTION | IMPREGNATION AMOUNT (ml) | DRYING T(°C) | DRYING DURATION (h) | CALCINATION T(°C) | CALCINATION DURATION (h) |
|---|---|---|---|---|---|---|---|---|---|
| 1 | C | 0,8 | 1300 | $S_1$ | 650 | 20–200 200 | 2 2 | 200–400 400 | 2 1 |
| 2 | A | 12,5* | 1260 | $S_1$ | 600 + 30 ml $H_2O$ | id | id | id | id |
| 3 | C | 0,8 | 1000 | $S_3$ | 500 | id05788id | | id | id |
| 3 | C Impregnated. | | 1080 | $S_3$ | 450 | id | id | id | id |
| 4 | D | 0,6 | 1250 | $S_1$ | 650 | id | id | id 350 | id 1 |
| 5 | E | 0,7 | 1330 | $S_1$ | 650 | id | id | id 350 | id 1 |
| 6 | C | 0,8 | 1000 | $S_2$ | 470 | id | id | 200–400 400 | 2 1 |
| 7 | B | 12,0* | 1290 | $S_1$ | 600 + 30 ml $H_2O$ | id | id | id | id |

OBTAINED CATALYST

| EX | WEIGHT (g.) | ACTIVE PHASE composition | $S_{b.w.}$ | SPECIFIC SURFACE ($m^2/g$) | GRAIN TO GRAIN CRUSHING (kg/mm) |
|---|---|---|---|---|---|
| 1 | 1560 | Mo/Fe = 2 | 16,8 | 12 | 3 |
| 2 | 1519 | " | 16,2 | 11 | 14* |
| 3 | 1080 | Mo/Fe = 2,5 | | 11 | 2 |
|   | 1150 | | 13,2 | | |
| 4 | 1505 | Mo/Fe = 2 | 16,6 | 14 | 2,5 |
| 5 | 1580 | " | 15,8 | 17 | 2,8 |
| 6 | 1192 | $\frac{Mo+W}{Fe+Co} = 1,5$, & $\frac{W}{Mo+W} =$ $\frac{Co}{Fe+Co} = 0,1$ | 16,1 | 15 | 3,1 |
| 7 | 1549 | Mo/Fe = 2 | 15,7 | 13 | 14,5* |

*Crushing expressed in kgF (catalyst in balls)

TABLE II

| Ex. | Bath temperature (°C) | Hot point temperature (°C) | $CH_3OH$ conversion (%) | Formaldehyde selectivity (%) | Formaldehyde Yield (%) |
|---|---|---|---|---|---|
| 1 | 280 | 360 | 98,5 | 97,5 | 96 |
| 2 | 290 | 360 | 98,0 | 92 | 90,2 |
| 3 | 300 | 380 | 97,5 | 93,2 | 90,9 |
| 4 | 280 | 360 | 98,9 | 96 | 94,95 |
| 5 | 260 | 350 | 99,9 | 90,8 | 90,7 |
| 6 | 280 | 364 | 98,8 | 93,9 | 92,8 |
| 7 | 285 | 370 | 98,4 | 95 | 93,5 |

We claim:
1. A process for manufacturing an impregnated supported catalyst consisting essentially of a carrier and an active phase comprising mainly molybdenum and iron in the form of oxides, in an atomic ratio of molybdenum/iron from 1.5 to 5, comprising a first step of preparing an impregnation solution containing, as metal elements, mainly molybdenum and iron, by introducing into a mixture of water with at least one alkanolamine, a solid homogeneous complex, mainly associating $MoO_4^{2-}$ and $NO_3^-$ anions, $Fe^{3+}$ and $NH_4^+$ cations and water, the homogeneous solid complex used in the first step being an amorphous solid gel prepared by tained at a temperature between its freezing point and 20°C, said solutions being used in relative amounts corresponding to an atomic ratio of Mo/Fe from 1.5 to 5, thereby forming a pasty composition which is converted to an opaque rigid substance which, after maturation, becomes the desired amorphous solid gel, the alkanolamine content of said mixture being sufficient for dissolving said complex, the resulting impregnation solution being used in a second step for impregnating a carrier, said impregnated carrier being dried in a third step and then roasted in a fourth step, so as to obtain the final catalyst.

2. A process according to claim 1, comprising, in the first step, introducing into a mixture of water with at least one alkanolamine containing from 300 to 600 g of alkanolamine per liter, an amount of homogeneous solid complex which, expressed as metal oxide weight, is from 100 to 500 g per liter of said mixture.

3. A process according to claim 1 in which the alkanolamine is selected from the primary, secondary or tertiary alkanolamines containing from 2 to 12 carbon atoms.

4. A process according to claim 3, in which the alkanolamine is selected from monoethanolamine and diethanolamine.

5. A process according to claim 1, in which the preparation of the amorphous solid gel has been performed by replacing, in the ferric nitrate solution up to 50 % of the ferric ions by an equivalent atomic amount of simple cations selected from those of cobalt, nickel, manganese, chromium, scandium, yttrium and rare earth metals.

6. A process according to claim 1 in which the preparation of the amorphous solid gel has been conducted by replacing, in the ammonium molybdate solution, up to 50 % of the molybdenum anions by an equivalent atomic amount of oxygen-containing ions selected from those of chromium, tungsten, manganese, vanadium and uranium.

7. A process according to claim 1 in which the carrier used in the second step consists substantially of alumina, silica, alumina-silica, magnesia, alumina-magnesia, magnesia-silica, alumina-magnesia-silica or a calcined clay and has a pore volume from 30 to 100 ml per 100 g and a specific surface of 1 to 20 m²/g.

8. A process according to claim 7, in which the carrier consists essentially of α-alumina or calcined clay.

9. A process according to claim 8, in which the carrier consists essentially of kaolinite calcined at 600°–900°C.

10. A process according to claim 1 in which, in the third step, the impregnated carrier is dried at a temperature from 50° to 150°C and then calcined at a temperature from 300° to 450°C.

11. A process according to claim 1 in which the carrier is used in the form of balls or extrudates.

12. A process according to claim 1 in which the carrier is used in a powdered form and is put in its final shape after impregnation, drying and calcination.

13. A catalyst as obtained by a process according to claim 1.

14. A catalyst according to claim 13, having an active phase content from 5 to 35 % by weight.

15. A catalyst according to claim 14, having an active phase content from 10 to 20 % by weight.

16. A catalyst according to claim 13 in the form of extrudates, having a resistance to crushing from 1 to 5 kg/mm.

17. A catalyst according to claim 13 in the form of balls, having a resistance to crushing higher than 10 kgF.

18. A process for manufacturing an impregnated supported catalyst consisting essentially of a carrier and an active phase comprising mainly molybdenum and iron in the form of oxides, in an atomic ratio of molybdenum/iron from 1.5 to 5, comprising a first step of preparing an impregnation solution containing, as metal elements, mainly molybdenum and iron, by introducing into a mixture of water with at least one alkanolamine, a solid homogeneous complex, mainly associating $MoO_4^{2-}$ and $NO_3^-$ anions, $Fe^{3+}$ and $NH_4^+$ cations and water, the homogeneous solid complex used in the first step being an amorphous solid gel prepared by a process in which there is performed, by mechanical trituration, the reaction between mainly a solid ammonium molybdate or freshly precipitated molybdic anhydride and solid ferric nitrate, in the presence of a water amount lower than the sum of the required amounts for forming saturated solutions of the reactants and at a temperature between the freezing point of said saturated solutions and 150°C, the reactants being used in relative amounts corresponding to an atomic ratio of Mo/Fe from 1.5 to 5, thereby forming a viscous solution or a homogeneous paste which, by maturation, is converted to the desired amorphous solid gel, the alkanolamine content of said mixture being sufficient for dissolving said complex, the resulting impregnation solution being used in a second step for impregnating a carrier, said impregnated carrier being dried in a third step and then roasted in a fourth step, so as to obtain the final catalyst.

19. A process according to claim 18, in which the preparation of the amorphous solid gel has been performed by replacing, in the mixture of reactants up to 50 % of the ferric ions by an equivalent atomic amount of simple cations selected from those of cobalt, nickel, manganese, chromium, scandium, yttrium and rare earth metals.

20. A process according to claim 18 in which the preparation of the amorphous solid gel has been conducted by replacing, in the mixture of the reactants, up to 50 % of the molybdenum anions by an equivalent atomic amount of oxygen-containing ions selected from those of chromium, tungsten, manganese, vanadium and uranium.

21. A process according to claim 18, comprising, in the first step, introducing into a mixture of water with at least one alkanolamine containing from 300 to 600 g of alkanolamine per liter, an amount of homogeneous solid complex which, expressed as metal oxide weight, is from 100 to 500 g per liter of said mixture.

22. A process according to claim 18, in which the alkanolamine is selected from the primary, secondary or tertiary alkanolamines containing from 2 to 12 carbon atoms.

23. A process according to claim 18, in which the alkanolamine is selected from monoethanolamine and diethanolamine.

24. A process according to claim 18 in which the carrier used in the second step consists essentially of alumina, silica, alumina-silica, magnesia, alumina-magnesia, magnesia-silica, alumina-magnesia-silica or a calcined clay and has a pore volume from 30 to 100 ml per 100 g and a specific surface of 1 to 20 m²/g.

25. A process according to claim 18, in which the carrier consists essentially of α-alumina or calcined clay.

26. A process according to claim 18, in which the carrier consists essentially of kaolinite calcined at 600°–900°C.

27. A process according to claim 18 in which in the third step, the impregnated carrier is dried at a temperature from 50° to 150°C and then calcined at a temperature from 300° to 450°C.

28. A process according to claim 18 in which the carrier is used in the form of balls or extrudates.

29. A process according to claim 18 in which the carrier is used in a powdered form and is put in its fianl shape after impregnation, drying and calcination.

30. A catalyst as obtained by a process according to claim 18.

31. A catalyst according to claim 30, having an active phase content from 5 to 35% by weight.

32. A catalyst according to claim 30, having an active phase content from 10 to 20% by weight.

33. A catalyst according to claim 30 in the form of extrudates, having a resistance to crusing from 1 to 5 kg/mm.

34. A catalyst according to claim 30 in the form of balls, having a resistance to crushing higher than 10 kgF.

35. A process for manufacturing an impregnated supported catalyst consisting essentially of a carrier and an active phase comprising mainly molybdenum and iron in the form of oxides, in an atomic ratio of molybdenum/iron from 1.5 to 5, comprising a first step of preparing an impregnation solution containing, as metal elements, mainly molybdenum and iron, by introducing into a mixture of water with at least one alkanolamine, a solid homogeneous complex, mainly associating $MoO_4^{2-}$ and $NO_3^-$ anions, $Fe^{3+}$ and $NH_4^+$ cations and water, the homogeneous solid complex used in the first step being a precipitate, mainly of iron molybdate, kneaded with a solution of an ammonium salt in an amount corresponding to 0.5–2 moles of ammonium salt per gram equivalent of iron contained in the precipitate, the alkanolamine content of said mixture being sufficient for dissolving said complex, the resulting impregnation solution being used in a second step for impregnating a carrier, said impregnated carrier being dried in a third step and then roasted in a fourth step, so as to obtain the final catalyst.

36. A process according to claim 35, in which the ammonium salt is a nitrate.

37. A process according to claim 35, comprising, in the first step, introducing into a mixture of water with at least one alkanolamine containing from 300 to 600 g of alkanolamine per liter, an amount of homogeneous solid complex which, expressed as metal oxide weight, is from 100 to 500 g per liter of said mixture.

38. A process according to claim 35 in which the alkanolamine is selected from the primary, secondary or tertiary alkanolamines containing from 2 to 12 carbon atoms.

39. A process according to claim 35, in which the alkanolamine is selected from monoethanolamine and diethanolamine.

40. A process according to claim 35 in which the carrier used in the second step consists essentially of alumina, silica, alumina-silica, magnesia, alumina-magnesia, magnesia-silica, alumina-magnesia-silica or a calcined clay and has a pore volume from 30 to 100 ml per 100 g and a specific surface of 1 to 20 m²/g.

41. A process according to claim 35, in which the carrier consists essentially of α-alumina or calcined clay.

42. A process according to claim 35, in which the carrier consists essentially of kaolinite calcined at 600°–900°C.

43. A process according to claim 35 in which, in the third step, the impregnated carrier is dried at a temperature from 50° to 150°C and then calcined at a temperature from 300° to 450°C.

44. A process according to claim 35 in which the carrier is used in the form of balls or extrudates.

45. A process according to claim 35 in which the carrier is used in a powdered form and is put in its final shape after impregnation, drying and calcination.

46. A catalyst as obtained by a process according to claim 35.

47. A catalyst according to claim 46, having an active phase content from 5 to 35% by weight.

48. A catalyst according to claim 46, having an active phase content from 10 to 20% by weight.

49. A catalyst according to claim 46 in the form of extrudates, having a resistance to crushing from 1 to 5 kg/mm.

50. A catalyst according to claim 46 in the form of balls, having a resistance to crushing higher than 10 kgF.

* * * * *

UNITED STATES PATENT AND TRADEMARK OFFICE
CERTIFICATE OF CORRECTION

PATENT NO. : 3,975,302

DATED : August 17, 1976

INVENTOR(S) : Philippe Courty et al.

It is certified that error appears in the above-identified patent and that said Letters Patent are hereby corrected as shown below:

[73] show read -- Assignee: INSTITUT FRANCAIS DU PETROLE --.

Signed and Sealed this

Fourth Day of January 1977

[SEAL]

Attest:

RUTH C. MASON
*Attesting Officer*

C. MARSHALL DANN
*Commissioner of Patents and Trademarks*